United States Patent [19]

Ott et al.

[11] Patent Number: 4,962,134
[45] Date of Patent: Oct. 9, 1990

[54] DENTAL IMPRESSION MATERIAL

[75] Inventors: Heidrun Ott, Wiesbaden-Auringen; Werner Kuhlmann, Mainz-Hechtsheim, both of Fed. Rep. of Germany

[73] Assignee: Blendax GmbH, Mainz, Fed. Rep. of Germany

[21] Appl. No.: 380,017

[22] Filed: Jul. 14, 1989

Related U.S. Application Data

[63] Continuation of Ser. No. 881,797, Jul. 3, 1986, Pat. No. 4,891,390.

[30] Foreign Application Priority Data

Jul. 13, 1985 [DE] Fed. Rep. of Germany ....... 3525054

[51] Int. Cl.$^5$ .................. A61K 6/10; C08G 77/06; A01N 1/02
[52] U.S. Cl. .................. 523/109; 264/16; 264/17; 427/2
[58] Field of Search ............... 523/109; 264/16, 17; 427/2

[56] References Cited

U.S. PATENT DOCUMENTS 4,673,354 6/1987 Culler .................................. 427/2
4,778,832 10/1988 Futami et al. ................... 523/109

Primary Examiner—Mark L. Bell
Assistant Examiner—David M. Brunsman
Attorney, Agent, or Firm—Birch, Stewart, Kolasch & Birch

[57] ABSTRACT

The present invention relates to the addition of aluminum salts of fatty acids with 12 to 18 carbon atoms, particularly aluminum stearate, to dental impression materials on the basis of addition and/or condensation crosslinking organosilicones to improve their structural viscosity behavior and thus to ease their handling for the dentist.

10 Claims, No Drawings

DENTAL IMPRESSION MATERIAL

This application is a continuation, of copending application Ser. No. 06/881,797 filed on July 3, 1986 now U.S. Pat. No. 4,891,390.

The present invention relates to a dental impression material on the basis of addition or condensation crosslinking silicones with improved properties of use.

Dental impression materials on the basis of addition or condensation crosslinking silicones are usually present in the form of pastes and contain, in addition to the organosilicones which polymerize or condensate when brought together with the co-system, inorganic fillers as well as possibly further additives like thixotropic agents. The co-system contains catalysts and crosslinking agents which-when brought together with the basic composition-cause curing of the system.

To achieve optimum impression properties it is necessary that both components are mixed exactly according to the working instructions.

In order to facilitate and guarantee the exact dosage, mixing in dental practice is normally done on a mixing block on which the stream lengths of the pastes to be observed are marked. In doing so, usually the problem arises that the observation of these dosage instructions is difficult because due to their viscosity the impression materials either run off, or, in case the of a highly viscous adjustment, the flowability of the mass is affected in such a way that handling is considerably difficult.

Thus, the problem led to the developing of a dental impression material on the basis of an organosilicone showing an optimum viscosity behavior not impeding the exact dosage.

The solution of this problem according to the invention consists in adding to such a dental impression material an aluminum mono-, -di- or tri-salt of a fatty acid with 12 to 18 C-atoms, preferably in an amount of 0.1 to 10% by weight in relation to the total composition, particularly 0.5 to 5% by weight of the silicone impression material.

The preferred aluminum salt is aluminum mono-, -di- or tri-stearate, mixtures of all these three salts can be used.

Also suitable for use are the corresponding aluminum salts of lauric, myristic or palmitic acid; but also aluminum salts of mixed fatty acids can be used.

By adding these aluminum salts, particularly aluminum salts, of stearic acid, a marked structural viscosity is imparted to the silicone impression material which permits exact dosing on the mixing block without running. On the other hand, due to the applied shearing force the paste becomes so fluid when mixed with the hardener component that formation of very detailed impressions is possible.

Another advantage of the dental impression materials according to the invention compared with the thixotropic systems known from the prior art is that they are able to rebuild the viscosity after strong shear stress, as it occurs e.g., in the dosage cylinder of a filling machine.

The application of the dental impression materials composed according to the invention is particularly advantageous in the preparation of correction impressions.

The addition or condensation crosslinking organosilicones generally used in dental impression materials are known per se.

The first group mainly consists of polydimethyl siloxanes containing vinyl groups and hydrogen polydimethyl siloxanes.

In this case the of a catalyst is necessary for curing. Particularly catalysts containing platinum, rhodium compounds, or metal carbonyls such as cobalt and manganese carbonyl are used.

Catalysts containing Platinum are preferred.

Condensation crosslinking organosilicones are polydiorganosiloxanes containing hydroxyl groups. These may be substituted by alkyl, cycloalkyl and aryl groups. Since the expert knows these substances (see e.g. Published European Patent Application No. 16,988) a detailed enumeration is unnecessary.

The phase consisting of condensation crosslinking organosilicones containing an inorganic filler is cured before use by reaction with a mixture of catalyst and crosslinking agent.

Also these crosslinking agents are well-known, usually these are O-silicone esters and polysilicone esters; also silane crosslinking agents may be added.

As the crosslinking reaction always takes place in the presence of a catalyst, such a catalyst must be added to the phase containing the crosslinking agent.

Suitable catalysts are metallic salts of optionally alkyl substituted carboxylic acids, particularly dibutyl stannous dilaurate, dibutyl stannous diacetate, dioctyl stannous di(2-ethylhexylhexanoate), or tetrabutyl titanate, lead laurate, etc..

The amount of catalyst is usually between 0.1 to 5 % by weight calculated to condensation crosslinking organosilicone.

The compositions containing addition and/or condensation crosslinking organosilicones, preferably present in the form of a paste, contain a considerable amount of preferably mineral fillers, such as quartz powder, colloidal silicas, calcium silicate, calcium carbonate, calcium sulfate, aluminum oxide and aluminum hydroxide, etc. Of course, also mixtures of different fillers can be used.

A survey on the composition and application of dental silicone impression materials can be found in the Monography of H. J. Rehberg, "Die Quintessenz der zahnärztlichen Abformhilfsmittel" (2nd Ed. 1978), particularly p. 70-83.

The surprising improvement of the properties of the silicone impression materials made according to the invention is impressively confirmed by the comparative tests described in the following, which show that when using aluminum stearate an optimum adjustment of the structural viscosity of the mass is possible, while with other polyvalent metallic salts like calcium, zinc, and magnesium stearate this effect could not be effected.

A basic formula of the following composition

| | |
|---|---|
| Christobalite | 36,5 (% by weight) |
| Calcium carbonate | 3,0 |
| Colloidal silica | 1,0 |
| w-Dihydroxy polydimethyl siloxane | 50,0 |
| Polydimethyl siloxane | 7,5 |
| Stearic acid salt | 2,0 | was examined concerning its viscosity behavior.

Alternatively, aluminum tristearate, zinc distearate, calcium distearate, and magnesium distearate were used as stearic acid salts and the viscosities of the respective compositions were determined.

The results were as follows:

|  | Al tristearate | Zn distearate | Ca distearate | Mg distearate |
| --- | --- | --- | --- | --- |
| Viscosity at 32 r.p.m. | 16,900 mPas | 14,400 mPas | 14,600 mPas | 14,400 mPas |
| Viscosity at 8 r.p.m. | 34,500 mPas | 18,100 mPas | 18,100 mPas | 16,500 mPas |

These results prove that surprisingly a satisfactory adjustment of the structural viscosity was only possible with the aluminum fatty acid salt.

In the following several examples of dental impression materials composed according to the invention the same, may be cured as usual after addition of a composition containing a catalyst and a crosslinking agent.

| A. Condensation crosslinking silicone impression materials | | |
| --- | --- | --- |
|  | Example 1 % by weight | Example 2 % by weight |
| α,w-Dihydroxy polydimethyl siloxane | 45,0 | 45,0 |
| Polydimethyl siloxane | 12,5 | 8,0 |
| Starch | — | 8,0 |
| Calcium carbonate | 3,0 | 3,0 |
| Quartz powder | 36,0 | 30,0 |
| Aluminum stearate mixture | 2,0 | 2,0 |
| Colloidal silica | 1,0 | 2,0 |
| Dyestuff | 0,5 | 2,0 |

The pastes are cured in the normal way by mixing with hardener paste or hardener liquid.

| B. Addition crosslinking silicone impression materials | | | | |
| --- | --- | --- | --- | --- |
|  | Example 1 | | Example 2 | |
|  | Basis paste % by weight | Catalyst paste | Basis paste | Catalyst paste |
| Vinyl end-stopped polydimethyl siloxane | 45,0 | 50,0 | 30,0 | 42,0 |
| Dimethylhydrogensilyl end-stopped polydimethyl siloxane | 5,0 | — | 10,0 | — |
| Pt siloxane complex | — | 0,02 | — | 0,01 |
| Aluminum stearate (mono-, di-, tristearate) | 2,0 | 2,0 | 1,5 | 1,5 |
| Quartz powder | 40,0 | 40,0 | 50,0 | 50,0 |
| Calcium carbonate | 5,5 | 5,48 | 8,0 | 5,99 |
| Colloidal silica | 2,0 | 2,0 | — | — |
| Dyestuff | 0,5 | 0,5 | 0,5 | 0,5 |

When both pastes are brought together, curing takes place in the known way.

We claim:

1. A method of making a dental impression which comprises:
    (a) mixing at least one crosslinkable organo-silicone, at least one aluminum salt of a $C_{12}$–$C_{18}$ fatty acid, and an inorganic filler to form a first phase;
    (b) mixing a catalyst and a crosslinking agent to form a second phase;
    (c) mixing said first phase with said second phase to form a dental impression material composition; and
    (d) making said dental impression.

2. The method according to claim 1, wherein said aluminum salt is selected from the group consisting of aluminum mono-, di-and tri-stearate.

3. The method according to claim 1, wherein said inorganic filler is selected from the group consisting of quartz powder, colloidal silica, calcium stearate, calcium carbonate, calcium sulfate, aluminum oxide, aluminum hydroxide and mixtures thereof.

4. The method according to claim 1, wherein said crosslinkable organosilicone is a polydiorgano siloxane containing hydroxyl groups.

5. The method according to claim 1, wherein said crosslinkable organosilicone is crosslinked by addition or condensation crosslinking.

6. The method according to claim 1, wherein said aluminum salt is present in an amount of from 0.1 to 10% by weight of said total composition.

7. The method according to claim 6, wherein said aluminum salt is present in an amount of from 0.5 to 5% by weight of said total composition.

8. The method according to claim 1, wherein said catalyst is a metallic salt, a carboxylic acid, or an alkyl substituted carboxylic acid.

9. The method according to claim 1, wherein said catalyst is present in an amount of from 0.1 to 5% by weight based on the amount of said crosslinkable organosilicone.

10. In a method for making a dental impression with a dental impression composition the improvement comprising:
    (a) mixing at least one crosslinkable organo-silicone, at least one aluminum salt of a $C_{12}$–$C_{18}$ fatty acid, and an inorganic filler to form a first phase;
    (b) mixing a catalyst and a crosslinking agent to form a second phase; and
    (c) mixing said first phase with said second phase to form said dental impression composition.

* * * * *